United States Patent
Lewis et al.

(10) Patent No.: US 6,407,276 B1
(45) Date of Patent: Jun. 18, 2002

(54) METHOD FOR IMPROVING SELECTIVITY FOR DIALKYLDICHLOROSILANE

(75) Inventors: Larry Neil Lewis, Scotia; Robert Edgar Colborn, Niskayuna; John Matthew Bablin, Amsterdam, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/820,025

(22) Filed: Mar. 29, 2001

(51) Int. Cl.⁷ .................................................. C07F 7/16
(52) U.S. Cl. .................................. 556/472; 252/183.13
(58) Field of Search ...................... 556/472; 252/183.13

(56) References Cited

U.S. PATENT DOCUMENTS

| | | |
|---|---|---|
| 2,380,995 A | 8/1945 | Rochow |
| 2,380,996 A | 8/1945 | Rochow et al. |
| 2,380,997 A | 8/1945 | Patnode |
| 2,389,931 A | 11/1945 | Reed et al. |
| 2,427,605 A | 9/1947 | Hurd |
| 2,464,033 A | 3/1949 | Gilliam |
| 2,473,260 A | 6/1949 | Rochow et al. |
| 3,446,829 A | 5/1969 | Zock |
| 4,824,984 A * | 4/1989 | Klar et al. ................. 556/472 |
| 4,864,044 A * | 9/1989 | Lewis et al. ................. 556/472 |
| RE33,452 E | 11/1990 | Ward, III et al. |
| 4,973,725 A * | 11/1990 | Lewis et al. ................. 556/472 |
| 5,117,030 A * | 5/1992 | Cattoz et al. ................. 556/472 |
| 5,338,876 A * | 8/1994 | Jung et al. ............... 556/472 X |
| 5,714,131 A * | 2/1998 | Margaria et al. ........ 556/472 X |

FOREIGN PATENT DOCUMENTS

EP 0 348 902 3/1995

OTHER PUBLICATIONS

Lewis et al., Catalyzed Direct Reactions of Silicon, 1993, Elsevier Science Publishers, B.V., pp. 1–66.
Eugene G. Rochow, The Direct Synthesis of Organosilicon Compounds, 1945, pp. 963–965, vol. 67.

* cited by examiner

Primary Examiner—Paul F. Shaver
(74) Attorney, Agent, or Firm—Bernadette M. Bennett; Noreen C. Johnson

(57) ABSTRACT

A method for forming a dialkyldichlorosilane, comprising reacting elemental silicon with an alkyl chloride using copper as a catalyst together with promoters zinc, tin, and a special promoter. The special promoter is silver, a silver compound, gold, a gold compound, or combinations thereof. The alkyl may be methyl such that the dialkyldichlorosilane is dimethyldichlorosilane and the alkyl chloride is methyl chloride. The reacting generates the dialkyldichlorosilane in accordance with a first selectivity for the dialkyldichlorosilane that exceeds a second selectivity for the dialkyldichlorosilane. The second selectivity is a selectivity for the dialkyldichlorosilane that would have existed had the special promoter been absent.

37 Claims, 11 Drawing Sheets

METHOD FOR IMPROVING SELECTIVITY FOR DIALKYLDICHLOROSILANE

BACKGROUND OF THE INVENTION

The present invention provides a method for improving selectivity for dialkyldichlorosilane product resulting from reacting silicon with an alkyl chloride.

Dialkyldichlorosilanes such as dimethyldichlorosilane are used commercially in the manufacture of methylsilicone polymers that are starting materials for methylsilicone sealants and heat cured rubber. Rochow, U.S. Pat. No. 2,380, 995, disclosed a method of preparing dimethyldichlorosilane ($Me_2SiCl_2$) using a direct reaction between methyl chloride (MeCl) and elemental silicon (Si) in the presence of a copper (Cu) catalyst in 1945. It is now a common practice to generate dimethyldichlorosilane by reacting silicon with methyl chloride using copper as a catalyst together with the promoters zinc (Zn) and tin (Sn). With concentrations by weight, based on silicon, of Cu (1–5%), Zn (0.04–20%), and Sn (5–30) ppm, the following reaction product mixture and associated weight percents is typically obtained with reaction temperatures below about 290–300° C.

- $Me_2SiCl_2$ ("Di") (80–93%);
- $MeSiCl_3$ ("Tri") (5–10%);
- $Me_3SiCl$ (1–5%);
- $MeHSiCl_2$ (0.5–3%);
- $Me_2HSiCl$ (0.1–1%);
- Other low boilers (0.1–0.5%);
- Residue (0.5–5%).

From the preceding table, the selectivity for dimethyldichlorosilane ($Me_2SiCl_2$) relative to methyltrichlorosilane ($MeSiCl_3$) in the product mixture is high. A high selectivity for dimethyldichlorosilane results when copper (Cu), zinc (Zn), and tin (Sn) have the following generally used concentrations by weight, based on silicon: Cu (0.5% to 5%), Zn (0.01% to 0.5%), and Sn (5 ppm to 100 ppm).

Unfortunately, the selectivity for dimethyldichlorosilane is reduced if the Cu, Zn, or Sn concentrations exceed the generally used concentrations or if the reaction temperature exceeds 300° C. In particular, the selectivity for dimethyldichlorosilane is substantially reduced if the copper concentration by weight exceeds 5%. However, if waste products of the reaction are recycled back into the reaction, the copper level will exceed 5% and may rise to as high as 25–30%. Additionally, it may be desirable to have the reaction occur at a temperature higher than 300° C. in order to increase the reaction rate.

Thus, there is a need to improve selectivity for dimethyldichlorosilane when the copper weight percent exceeds 5% based on silicon or the reactor temperature is higher than 300° C.

BRIEF SUMMARY OF THE INVENTION

The present invention provides a method for forming a dialkyldichlorosilane, comprising reacting at a reaction temperature elemental silicon with an alkyl chloride using copper as a catalyst together with promoters zinc, tin, and a special promoter comprising silver, a silver compound, gold, a gold compound, or combinations thereof.

The present invention provides a chemical mixture used in a chemical reaction that generates a dialkyldichlorosilane, said chemical mixture comprising reactants, a catalyst, and promoters, wherein the reactants include elemental silicon and an alkyl chloride, wherein the catalyst includes copper, wherein the promoters include zinc, tin, and a special promoter comprising silver, a silver compound, gold, a gold compound, or combinations thereof, and wherein the chemical reaction is executed at a reaction temperature.

The present invention improves selectivity for dimethyldichlorosilane when the copper weight percent exceeds 5% based on silicon or the reactor temperature is higher than 300° C.

DETAILED DESCRIPTION OF THE INVENTION

Figure 1:
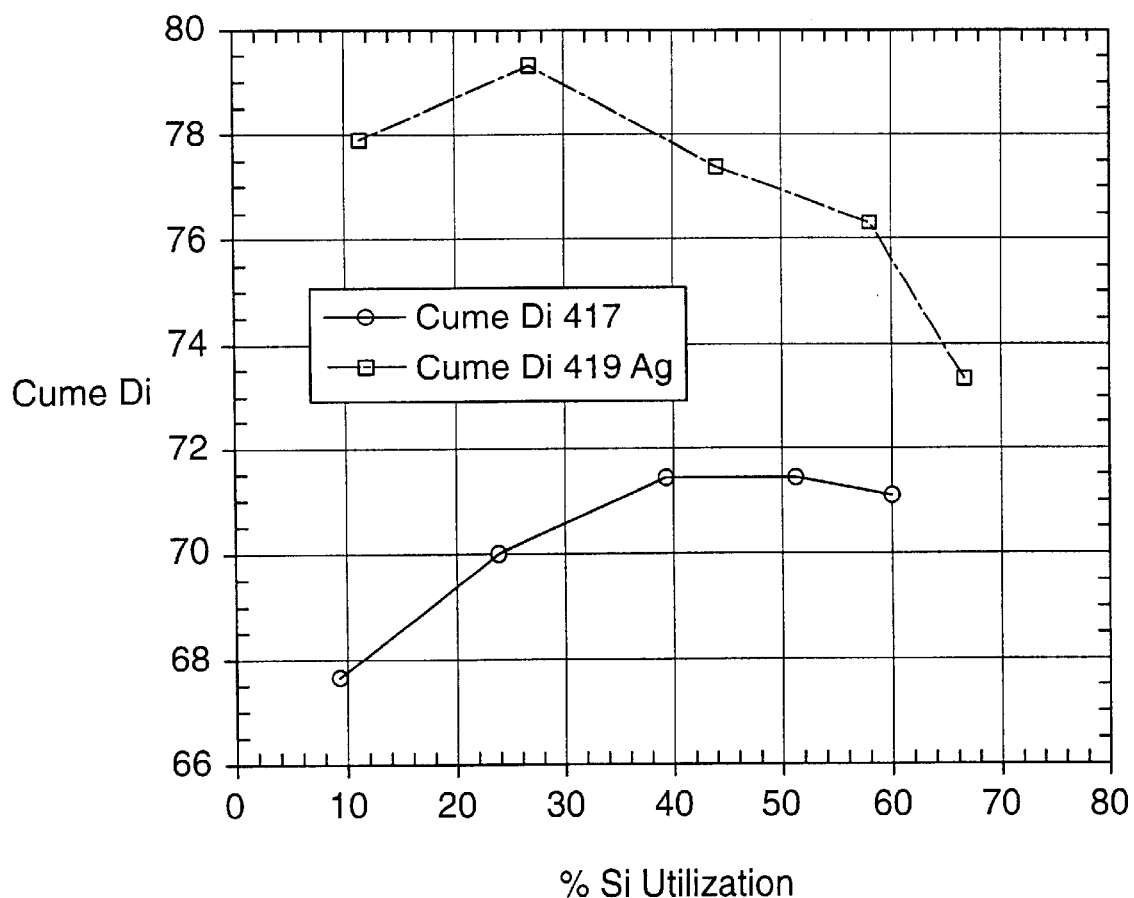
FIG. 1 depicts plots showing an effect of addition of 500 ppm silver (Ag) (#419 with Ag vs. #417 without Ag) on cumulative selectivity for dimethyldichlorosilane at a reaction temperature of 310° C., said selectivity based on a dimethyldichlorosilane weight percent, in accordance with embodiments of the present invention.

The present invention provides a method and structure for improving selectivity for dialkyldichlorosilane product that is produced by reacting elemental silicon (Si) with an alkyl chloride, using copper (Cu) as a catalyst together with the promoters zinc (Zn) and tin (Sn) by adding a special promoter to the reacting mixture.

Adding the special promoter improves selectivity for dialkyldichlorosilane in the product mixture, based on the dialkyldichlorosilane weight percent or the alkyltrichlorosilane/dialkyldichlorosilane weight percent ratio. Thus, the reacting mixture of the present invention includes silicon, alkyl chloride, copper, zinc, tin, and the special promoter. The special promoter may be elemental silver (Ag), a silver compound, elemental gold (Au), a gold compound, or combinations thereof. Elemental silver or elemental gold used as the special promoter may be in any of various forms such as, for example, powders, flakes, solders, colloids, and the like. Silver compounds used as the special promoter include silver halides (for example, silver chloride, silver bromide and silver iodide), silver carbonate, silver oxides, silver carbonate, silver nitrate, and like silver compounds. A concentration of the special promoter in a range between about 10 ppm and about 5000 ppm by weight based on silicon is effective for improving selectivity for the dialkyldichlorosilane. A more typical concentration of the special promoter is in a range between about 50 ppm and about 2500 ppm by weight based on silicon, and a most typical concentration is in a range between about 100 ppm and about 1000 ppm by weight based on silicon.

Assuming that the special promoter (silver, a silver compound, gold, a gold compound, or combination thereof) is present in the reacting mixture, other promoters may be added to the reacting mixture. Such other promoters include phosphorus compounds (e.g., copper phosphide, antimony, phosphines, for example, trichlorophosphine). If a phosphorus compound is present, the concentration of the phosphorus compound would be in a range between about 50 ppm and about 1000 ppm by weight based on silicon.

The alkyl chloride of the reacting mixture include, but are not limited to, methyl, ethyl, n-propyl, n-butyl, isopropyl, isobutyl, sec-butyl, tert-butyl, n-pentyl, etc. Additionally, the alkyl chloride may have unsaturation (e.g., vinyl chloride, alkyl chloride) or have varying chloride substitutions (e.g., methylene chloride). Thus if the alkyl group is methyl, then the dialkyldichlorosilane in the product mixture includes methylchlrosilanes such as dimethyldichlorosilane (Di), which is the preferred methyldichlorosilane, and a variety of other silanes such as tetramethylsilane, trimethylchlorosilane, methyltrichlorosilane (Tri), silicon tetrachloride, trichlorosilane, and methyldichlorosilane.

The copper may be in various forms including, but not limited to, a carboxylic salt of copper (e.g., copper formate, copper acetate), a copper oxide (e.g., CuO, $Cu_2O$), a copper halide (e.g., cuprous chloride, cupric chloride), and elemental chloride in the form of flake or powder. The copper may also be drawn from waste streams (e.g., spent methyldichlorosilane beds or ejected fine particles from a methyldichlorosilane bed). Typically, the copper is present in a range between about 0.5% and about 20% by weight based on silicon. Waste streams may have copper in a range between about 10% and about 30% by weight based on silicon.

The zinc may include, for example, zinc metal, zinc dust, zinc powder, zinc halide (e.g., zinc chloride), and zinc oxide. The tin may include, for example, tin dust, tin halide (e.g., tin tetrachloride), tin oxide, tetraalkyl tin (e.g., tetramethyl tin), and organo tin halide. Either or both of the zinc and the tin can be present as alloyed with the copper as brass or bronze. Both tin and zinc can be derived from a spent methyldichlorosilane bed or include ejected fine particles from a methyldichlorosilane bed.

Dimethyldichlorosilane ($Me_2SiCl_2$) is highly valuable commercially and it is thus desirable to maximize the production and selectivity of dimethyldichlorosilane. Methylchlorosilanes, which include dimethyldichlorosilane, may be manufactured in a fluid bed reactor in a continuous manner or in a batch reaction. In the reaction of the present invention, gaseous methyl chloride (MeCl) is flowed over a solid mixture of elemental silicon, copper, zinc, tin, and the special promoter (e.g., silver, a silver compound, gold, a gold compound, or combination thereof) such that the methyl chloride reacts with the elemental silicon to form a product mixture of methylchlorosilanes that includes dimethyldichlorosilane. The reaction of the present invention increases the selectivity of dimethyldichlorosilane relative to the selectivity of dimethyldichlorosilane that would otherwise prevail in an absence of the special promoter.

Silicon is usually obtained at a purity of at least 98% by weight of silicon and is then comminuted to particles of silicon before being fed into an appropriate reactor as needed. Although a fluidized bed is preferred, the process of the present invention can be utilized in other types of reactors, such as fixed bed and a stirred bed. A fluidized reactor typically yields a better selectivity and quantity of methyldichlorosilane products than does a fixed bed or stirred bed reactor.

Methyl chloride or an inert gas such as argon, or mixture thereof, can be used to fluidize the bed of silicon particles in the reactor. The silicon present in the fluidized bed can have a particle size below 700 microns, with an average size of greater than 20 microns and less than 0.300 microns in size. The mean diameter of the silicon particles is typically in a range between about 100 microns and about 150 microns.

The gaseous crude reaction product mixture and entrained reaction particulates are passed out of the fluidized reactor and passed through one or more cyclones so as to separate the larger particles of materials from the reaction product mixture. The cyclones are devices that cause gas and fine dust to exit the reactor and larger particles to return to the reactor. The cyclone separation is often called elutriation. The smaller particles in the gas stream of the reaction product mixture are passed out with the methyldichlorosilane product mixture which includes the dimethyldichlorosilane. The product fractions of the reaction product mixture may be isolated, purified, and collected by any convenient means such by distillation. Once the product fractions are collected, the formation of dimethyldichlorosilane (Di) and methyltrichlorosilane (Tri) may be confirmed by such methods as gas chromatography (GC), gas chromatography-mass spectroscopy (GC/MS), and multinuclear magnetic resonance (NMR).

The larger, separated-out particles from the reaction product mixture, which are called "silicon fines," can be returned to the reactor for further utilization in the process so as to maximize a yield of dimethyldichlorosilane in accordance with a Percent Silicon Utilization. The Percent Silicon Utilization ("% Si Utilization") is the percentage of an initial quantity (by weight) of silicon that is consumed as the reaction proceeds in time. Thus, return to the reactor of these silicon fines for further utilization in the reactor contributes to the % Si Utilization.

Returning the silicon fines to the reactor to increase silicon utilization results in increasing some or all of the copper, zinc, and tin weight percents, based on silicon, to levels greater than about: 5% copper, 0.5% zinc, and 100 ppm tin, respectively. As stated earlier, such high levels of copper, zinc, and tin decrease selectivity for dimethyldichlorosilane. Such decrease in selectivity for dimethyldichlorosilane, however, is counteracted in accordance with the present invention by the addition of the special promoter (i.e., silver, a silver compound, gold, a gold compound, or combination thereof).

In order that those skilled in the art will be better able to practice the invention, the following Examples are given by way of illustration and not by way of limitation.

In the Examples, the reaction of elemental silicon with gaseous methyl chloride for generating dimethyldichliorosilane (Di) in the methylchlorosilane product mixture was carried out in a fixed bed reactor but could have been run in a stirred bed, fluidized bed, and the like. Solids comprising silicon, copper, zinc, tin, and other metals associated with the silicon (e.g., aluminum and iron) were charged into the reactor and then the methyl chloride gas was flowed over the solids. Products were collected using a condenser and analyzed by gas chromatography. All percentages stated in the Examples are weight percent and ppm are parts per million by weight based on silicon.

The plotted results of the Examples are expressed in terms of the following terminology and notation. Di and Tri represent dimethyldichlorosilane ($Me_2SiCl_2$) and methyltrichlorosilane ($MeSiCl_3$), respectively. "D" and "T" is the weight percent of dimethyldichlorosilane and methyltrichlorosilane, respectively, in the reaction product mixture. "D selectivity" is a selectivity for dimethyldichlorosilane in the product mixture, as measured by D. "T/D selectivity" is a selectivity for dimethyldichlorosilane in the product mixture, as measured by T/D. The D selectivity increases as D increases, while the T/D selectivity increases as T/D decreases. Additionally, MH is the weight percent of methyldichlorosilane ($MeHSiCl_2$) in the reaction product mixture. Since methyldichlorosilane is not considered to be desirable, the quality of the overall reaction product mixture increases as MH decreases.

A cumulative D selectivity, which is identified as "Cume Di," is expressed in the Examples in terms of the % Silicon Utilization. A cumulative T/D selectivity, which is identified as "Cume T/D," is likewise expressed in terms of the % Si Utilization. A cumulative MH, which is identified as "Cume MH" is also expressed in terms of the % Si Utilization.

EXAMPLE 1

The glass reactor was 100 millimeters (mm) long by 13 mm wide with a medium porosity glass frit located 80 mm from one end. Solids (i.e., silicon, copper, zinc, tin, etc.) were loaded into the glass reactor and then heated under a flow of argon. The time zero of an experiment was when the methyl chloride flow was turned on. The reaction product mixture was collected at a –20° C. condenser using a VWR model 1156 recirculating chiller. Methyl chloride flow was controlled with a MKS model 1179 mass flow controller using Kel F seals and a MKS type 247 four channel read out. A furnace used for heating the reactor was A Nichrome®-wire-wound glass tube heated in two zones with two separate Antech Sales model 59690 Watlow temperature controllers.

The solids loaded into the reactor comprised 3 grams (g) of a mixture "silicon fines" having silicon with 19.45% Cu, 1. 14% Zn, and 178 ppm Sni. The reactor was installed in the furnace and arg on flow was initiated. The bed was purged with argon for ½ hour at an argon flow rate of 40 cc/min. Heat was then turned on and typically within ½ hour, the bed temperature had stabilized at about 310° C. Then argon was turned off and methyl chloride flow at 35 cc/min was initiated.

Methylchlorosi lane vapor leaving the reactor was recovered with a –20° C. condenser. Methylchlorosilane vapor less past the condenser were negligible at the production rates usually encountered in this work.

Figure 2:
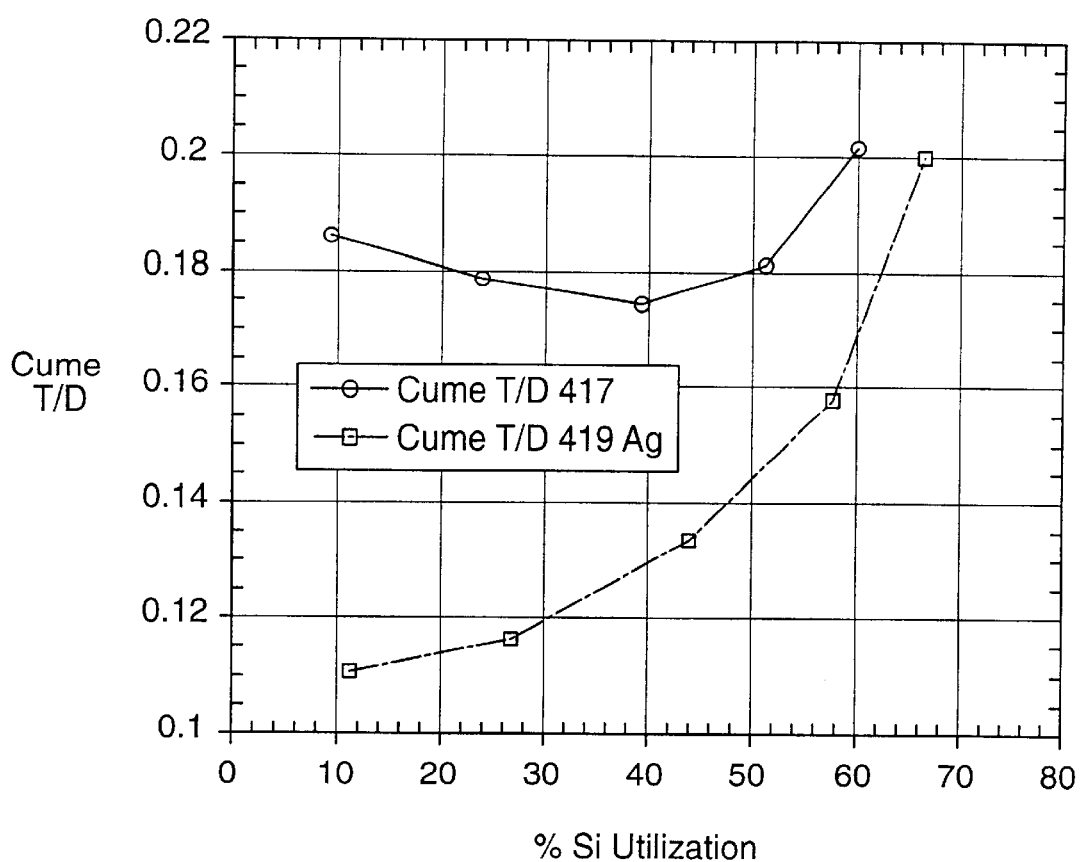
FIG. 2 depicts plots showing an effect of addition of 500 ppm Ag (#419 with Ag vs. #4.17 without Ag) on cumulative selectivity for dimethyldichlorosilane at a reaction temperature of 310° C., said selectivity based on a methyltrichlorosilane/dimethyldichlorosilane weight percent ratio (T/D), in accordance with embodiments of the present invention.

Liquid methylchlorosilane product mixture was periodically removed from the collector. The samples were weighed and later analyzed by GC. FIG. 1 depicts the Cume Di of Example 1 as plot "Cume Di 417," showing a cumulative D selectivity between about 67.5% and about 71.5% over a % Si Utilization range between about 10% and about 50%. FIG. 2 depicts the Cume Di of Example 1 as plot "Cume T/D 417," showing a cumulative T/D selectivity between about 0.176 and about 0.187 over a % Si Utilization range between about 10% and about 50%. Example 1 serves as a reference example against which Example 2 may be compared for the effect of adding silver as a promoter.

EXAMPLE 2

The experiment in Example 1 was repeated except that 1.5 milligrams (i.e., 500 ppm) of silver powder was pre-mixed with 3 grams of the silicon charge described in Example 1. An effect of adding 500 ppm silver powder under the conditions of Example 1 on the cumulative D selectivity is shown in FIG. 1 as the plot "Cume Di 419 Ag" showing a cumulative D selectivity between about 77% and about 79% over a % Si Utilization range between about 10% and about 50%. An effect of adding 500 ppm silver powder under the conditions of Example 1 on the cumulative T/D selectivity is shown in FIG. 2 as plot "Cume T/D 419 Ag" showing a cumulative T/D selectivity between about 0.11 and about 0.145 over a % Si Utilization range between about 10% and about 50%.

Thus, Examples 1 and 2 show that an addition of silver as a promoter increased the cumulative D selectivity by about 8 to about 15 percent, and the addition of silver improved the cumulative T/D selectivity by about 20 to about 40 percent, over the % Si Utilization range between about 10% and about 50% under the stated condition which include a 19.45 weight percent of copper and a reaction temperature of 310° C.

EXAMPLE 3

Figure 3:
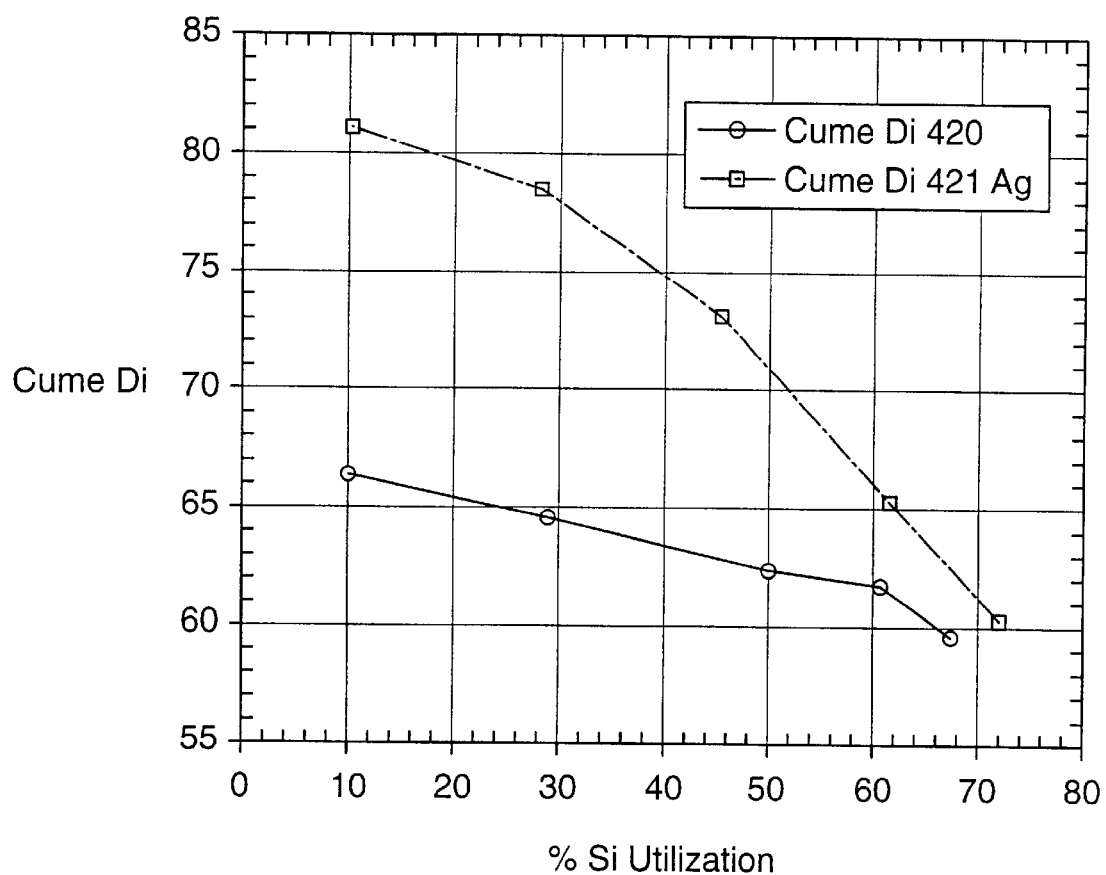
FIG. 3 depicts plots showing an effect of addition of 733 ppm Ag (#421 with Ag vs. #420 without Ag) on cumulative selectivity for dimethyldichlorosilane at a reaction temperature of 330° C., said selectivity based on a dimethyldichlorosilane weight percent, in accordance with embodiments of the present invention.
Figure 4:
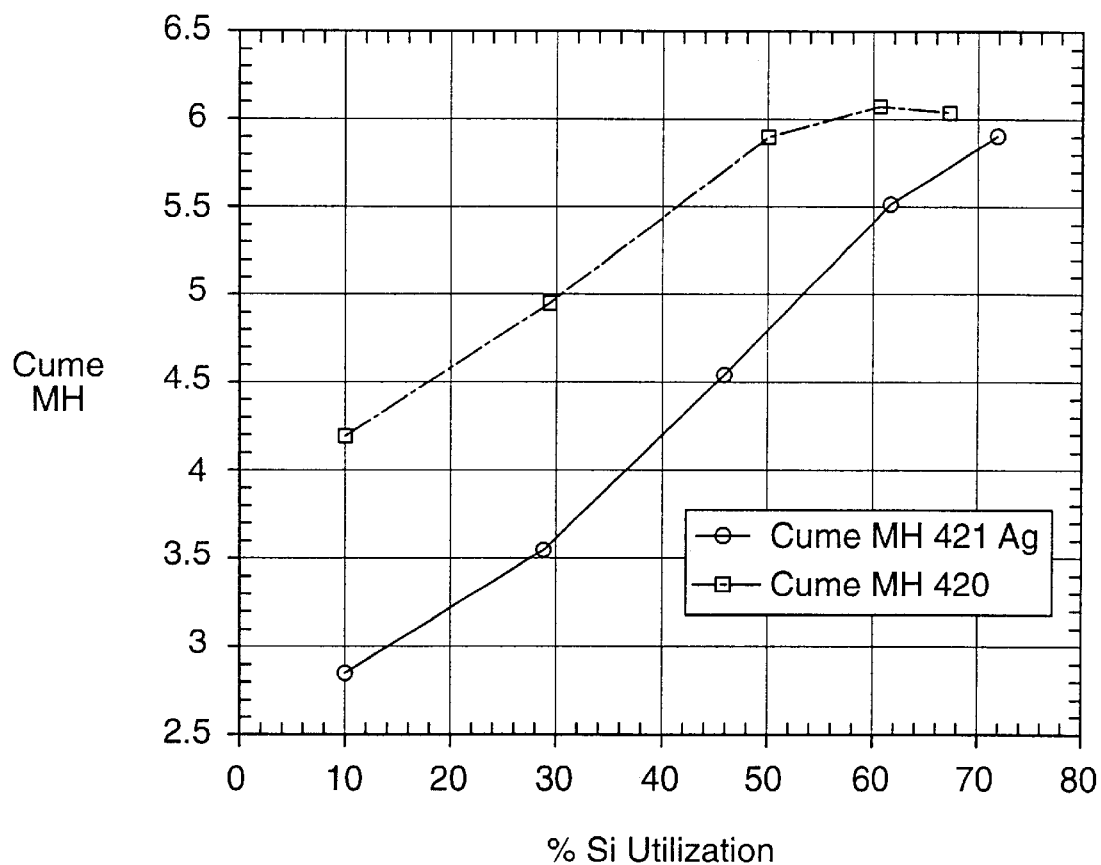
FIG. 4 depicts plots showing an effect of addition of 733 ppm Ag (#421 with Ag vs. #420 without Ag) on cumulative methyldichlorosilane at a reaction temperature of 330° C., based on a methyldichlorosilane weight percent, in accordance with embodiments of the present invention.

The experiment in Example 1 was repeated except that the temperature was 330° C. instead of310° C. FIG. 3 depicts the Cume Di of Example 3 as plot "Cume Di 420," showing a cumulative D selectivity between about 63% and about 67% over a % Si Utilization range between about 10% and about 50%, wherein the data from about 30% to about 50% Si Utilization was linearly extrapolated to 10% Si Utilization. FIG. 4 depicts the Cume MH of Example 3 as plot "Cume MH 420," showing a cumulative MH between about 4.2% and about 5.9% over a % Si Utilization range between about 10% and about 50%, wherein the data from about 30% to about 50% Si Utilization was linearly extrapolated to 10%

Figure 5:
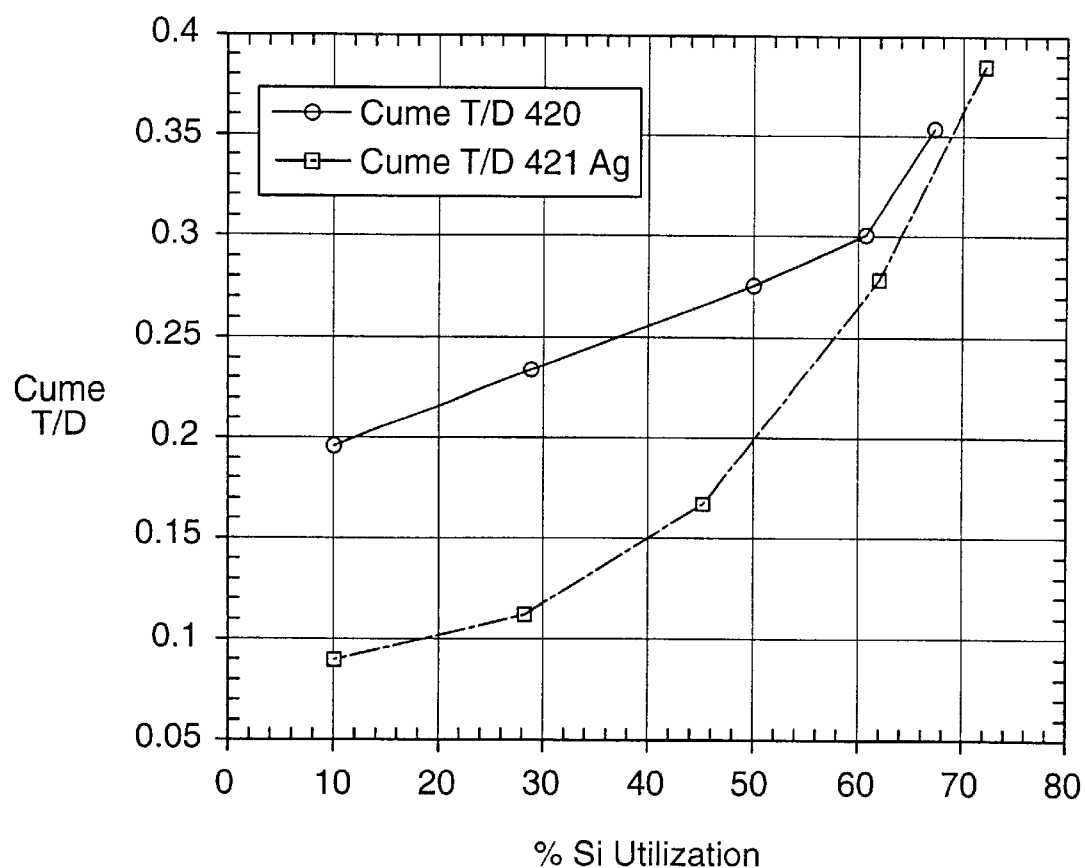
FIG. 5 depicts plots showing an effect of addition of 733 ppm Ag (#421 with Ag vs.# 420 without Ag) on cumulative selectivity for dimethyldichlorosilane at a reaction temperature of 330° C., said selectivity based on a methyltrichlorosilane/dimethyldichlorosilane weight percent ratio (T/D), in accordance with embodiments of the present invention.

Si Utilization. FIG. 5 depicts the Cume Di of Example 3 as plot "Cume T/D 421 Ag" showing a cumulative T/D selectivity between about 0.195 and about 0.275 over a % Si Utilization range between about 10% and about 50%, wherein the data from about 30% to about 50% Si Utilization was linearly extrapolated to 10% Si Utilization. Examples 3 serves as a reference example against which Example 4 may be compared for the effect of adding silver as a promoter.

EXAMPLE 4

The experiment in Example 3 was repeated except that 2.2 mg (i.e., 733 ppm) Ag powder was premixed with 3 grams of the silicon charge described in Example 3. An effect of adding 733 ppm silver powder under the conditions of Example 3 on the cumulative D selectivity is shown in FIG. 3 as plot "Cume Di 421 Ag" showing a cumulative D selectivity between about 71.5% and about 81% over a % Si Utilization range between about 10% and about 50%. An effect of adding 733 ppm silver powder under the conditions of Example 3. on the cumulative MH is shown in FIG. 4 as plot "Cume MH 421 Ag" showing a cumulative MH between about 2.8% and about 4.8% over a % Si Utilization range between about 10% and about 50%. An effect of adding 733 ppm silver powder under the conditions of Example 3 on the cumulative T/D selectivity is shown in FIG. 5 as plot "Cume T/D 421 Ag" showing a cumulative T/D selectivity between about 0.078 and about 0.195 over a % Si Utilization range between about 10% and about 50%.

Thus, Examples 3 and 4 show that an addition of silver as a promoter increased the cumulative D selectivity by about 13 to about 22 percent, reduced cumulative MH by about 19 to about 33 percent, and improved cumulative T/D selectivity by about 29 to about 60 percent, over the % Si Utilization range between about 10% and about 50% under the stated condition which include a 19.45 weight percent of copper. and a reaction temperature of 330° C.

When compared with Examples 1 and 2, the Examples 3 and 4 show that addition of silver as a promoter was more effective at 330° C. than at 310° C. in improving both cumulative D selectivity and cumulative T/D selectivity, over the % Si Utilization range between about 10% and about 50%.

EXAMPLE 5

Figure 6:
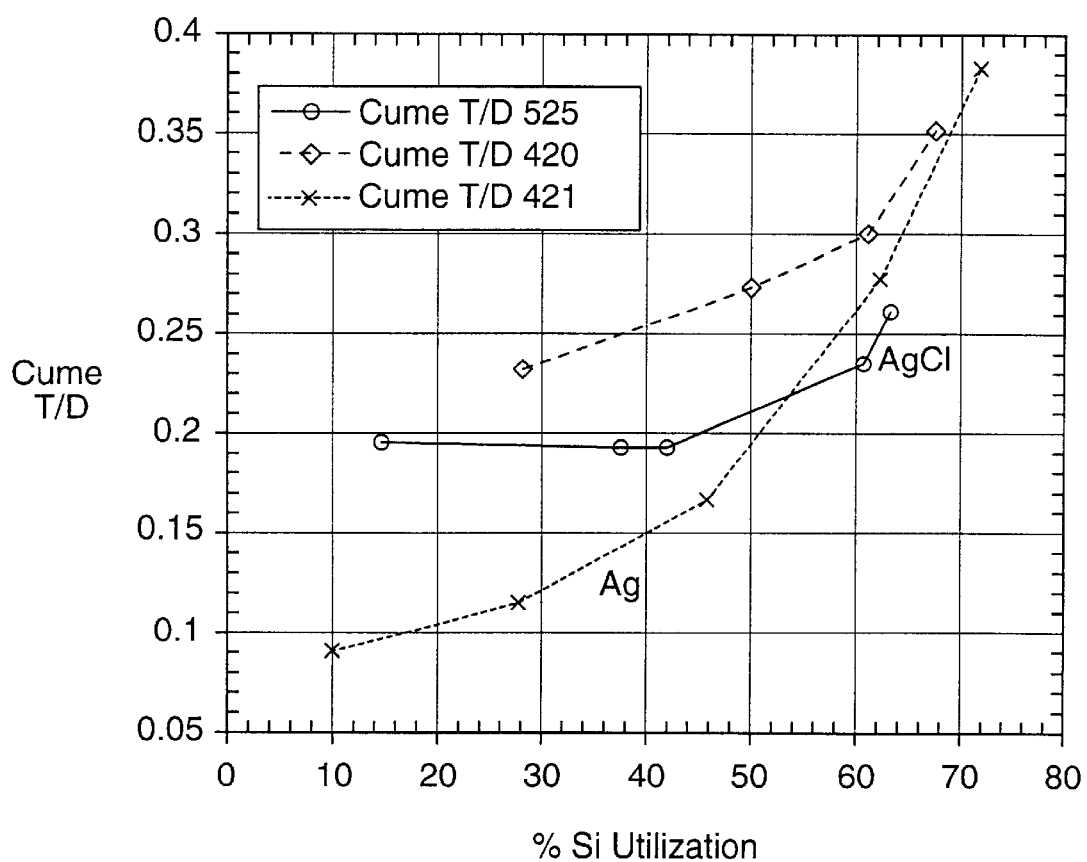
FIG. 6 depicts plots showing an effect of addition of 2033 ppm silver chloride (AgCl) (#525 with AgCl) on cumulative selectivity for dimethyldichlorosilane at a reaction temperature of 330° C., said selectivity based on a methyltrichlorosilane/dimethyldichlorosilane weight percent ratio (T/D), in accordance with embodiments of the present invention.

The experiment at 330° C. in Example 3 was repeated except that 6.1 mg (i.e., 2033 ppm) silver chloride (AgCl) powder, which corresponds to 1520 ppm Ag, was premixed with 3 grams of the silicon charge described in Example 3. FIG. 6 shows the cumulative T/D selectivity as "Cume T/D 525" (in relation to the AgCl addition), and additionally reproduced for comparison the "Cume T/D 421 Ag" and "Cume T/D 420" curves of FIG. 5 (in relation to the silver addition and the no special promoter addition, respectively). FIG. 6 shows that the cumulative T/D selectivity shown as "Cume T/D 525" with AgCl added was between about 0.195 and about 0.21 over a % Si Utilization range between about 10% and about 50%. From FIG. 6, the cumulative T/D selectivity with AgCl added was higher than the cumulative T/D selectivity with no special promoter added, over a %.Si Utilization range between about 10% and about 50%. Also from FIG. 6, the cumulative T/D selectivity with AgCl added was lower than the cumulative T/D selectivity with Ag added over a % Si Utilization range between about 10% and about 50%.

Figure 7:
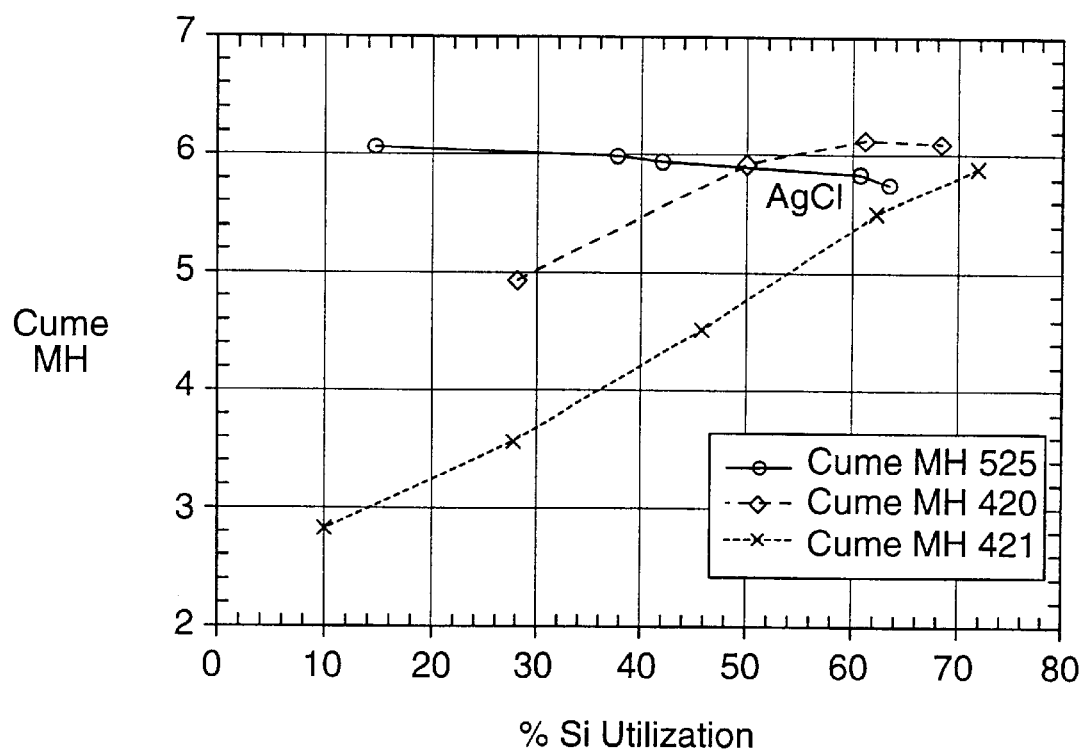
FIG. 7 depicts plots showing an effect of addition of 2033 ppm AgCl (#525 with AgCl) on cumulative methyldichlorosilane at a reaction temperature of 330° C., based on a methyldichlorosilane weight percent, in accordance with embodiments of the present invention.

FIG. 7 shows the cumulative MH as "Cume MH 525" (in relation to the AgCl addition), and additionally reproduces for comparison the "Cume MH 421 Ag" and "Cume MH 420" curves of FIG. 4 (in relation to the silver addition and the no special promoter addition, respectively). FIG. 7 shows that the cumulative MH shown as "Cume T/D 525" with AgCl added was between about 5.9% and about 6.1% over a % Si Utilization range between about 10% and about 50%. From FIG. 7, the cumulative MH with AgCl added was lower than the cumulative MH with no special promoter added over a % Si Utilization range between about 10% and about 50%. Also from FIG. 6, the cumulative MH with AgCl added was higher than the cumulative MH with Ag added, over a % Si Utilization range between about 10% and about 50%.

Thus, Example 5 shows that an addition of silver chloride as a promoter increased the cumulative T/D selectivity and decreased the cumulative MH over a % Si Utilization range between about 10% and about 50%.

EXAMPLE 6

The reaction of Example 1 was repeated except that the fixed bed reactor was charged with 6 g composite of silicon: pre-mixed with copper flake and brass in a weight ratio of 7:5. The brass was composed of 89.5% copper, 10% zinc and 0.5% tin by weight. The reaction was run at 310° C. with a MeCl flow of 35 mL/min. No special promoter (i.e., silver, a silver compound, gold, a gold compound, or combinations thereof) was added. Three replicate experiments were performed with 15% total Cu by weight, and the experiment was then repeated at 5% total Cu in the bed. Measurements of Cume T/D showed a higher Cume T/D, and thus a lower T/D selectivity, with 15% Cu as compared with the 5% Cu. In particular, Cume T/D for the 5% copper was determined by measurement to be in a range between about 0.07–0.12 when the % Si Utilization was in a range between about 10% and about 50%, while Cume T/D for the 15% copper was determined by measurement to be in a range between about 0.18 and about 0.55 when the % Si Utilization was in a range between about 10% and 50%.

Example 6 shows that increasing the weight percent of copper reduced the cumulative T/D selectivity. Nonetheless, Examples 1 and 2, which had a high copper weight percent of 19.45% and which has the same reaction temperature of 310° C. as Example 6, show that adding silver promoter counteracted the adverse effect of high copper by increasing the cumulative TED selectivity.

EXAMPLE 7

The reaction of Example 6 was repeated except that 5% Cu in the form of CuCl (0.3 g) was combined with silicon. Zinc (10 mg) and tin (0.3 mg) were also added to the 6 grams charged to the fixed bed reactor. Again, no special promoter (i.e., silver, a silver compound, gold, a gold compound, or combination thereof) was added. The experiment was performed at 300° C. and repeated at 330° C. Measurements of Cume T/D showed a higher Cume T/D, and thus a lower T/D selectivity, at 330° C. as compared with 300° C. In particular, Cume T/D at 300° C. was determined by measurement to be in a range between about 0.041 and about 0.044 when the % Si Utilization was in a range between about 10% and about 30%, while Cume T/D at 330° C. was determined by measurement to be in a range between about 0.043 and about 0.048 when the % Si Utilization was in a range between about 10% and about 30%.

Example 7 shows that increasing the temperature reduced the cumulative T/D selectivity when there was no special promoter (e.g., silver) present. In contrast, Examples 2 and 4 show that adding silver promoter counteracted the adverse effect of high reaction temperature by increasing the cumulative T/D selectivity to a greater extent at a reaction temperature at 330° C. than at a reaction temperature at 310° C.

EXAMPLE 8

Fluidized bed experiments were performed wherein 20 g of bed comprising 4 g of fines described in Example 1 and; 16 g of silicon were combined and charged to the reactor. Copper, zinc, and tin were present in concentration by weight of about 3.89%, 0.23%, and 36 ppm, respectively. A test reaction at 330° C. was initiated without any special promoter present. During the reaction, 100 ppm by weight silver powder was added at about 62% Silicon Utilization. Upon adding the 100 ppm silver, the cumulative D selectivity increased sharply from about 53% to about 69%, representing a 30% increase in cumulative D selectivity, as the % Silicon Utilization changed from about 62% to about 68%.

In summary, Examples 2, 4, and 8 have specifically demonstrated increases in cumulative D selectivity resulting from addition of in a range between about 100 ppm and about 733 ppm silver promoter. Interestingly, the increase in cumulative D selectivity was 30% with 100 ppm silver at 330° C. in Example 8, while the increase in cumulative D selectivity was 22% or less with 733 ppm silver at 330° C. in Example 3 as shown in Table 1. An extrapolation based on a linear relationship between increase in cumulative D selectivity and ppm silver results in a calculated increase in cumulative D selectivity if the ppm silver is as high as 2474 ppm silver. With the data presented and reasonable extensions thereof, a concentration in a range between about 10 ppm and about 5000 ppm by weight of the special promoter (e.g., silver) is considered to be effective for improving D selectivity or T/D selectivity. A preferred concentration of the special promoter is in a range between about 50 ppm and about 2500 ppm, and a most preferred concentration is in a range between about 100 ppm and about 1000 ppm.

EXAMPLE 9

A fixed bed reactor experiment is prepared as described in Example 2 except that in place of silver powder there is employed an equimolar amount of a gold powder. The D selectivity or T/D selectivity is improved compared to a fixed bed experiment without the compound shown.

FURTHER ANALYSIS OF EXAMPLES

The preceding analysis showed that adding silver promoter increased cumulative T/D selectivity when the reaction temperature exceeds 310° C. The following analysis, based on Tables 1 and 2, discussed below, extends the preceding analysis by showing that adding silver increases both D selectivity and cumulative T/D selectivity for reaction temperatures of at least about 280 to 290° C.

Table 1 summarizes Cume Di data from FIGS. 1 and 3 as follows.

TABLE 1

| % Si Util. | Reacted At 310° C. ($T_1$) | | | Reacted At 330° C. ($T_2$) | | | $T_{MIN}$ (° C.) |
|---|---|---|---|---|---|---|---|
| | Ag | No Ag | Ag/No Ag ($R_1$) | Ag | No Ag | Ag/No Ag ($R_2$) | |
| 10 | 77.5 | 67.5 | 1.15 | 81.0 | 67.0 | 1.21 | 260 |
| 20 | 78.5 | 69.5 | 1.13 | 79.5 | 66.5 | 1.20 | 272 |
| 30 | 79.0 | 70.5 | 1.12 | 78.5 | 64.5 | 1.22 | 286 |
| 40 | 77.8 | 71.5 | 1.09 | 75.0 | 63.5 | 1.18 | 290 |
| 50 | 77.0 | 71.5 | 1.08 | 71.5 | 63.0 | 1.13 | 278 |

Figure 8:
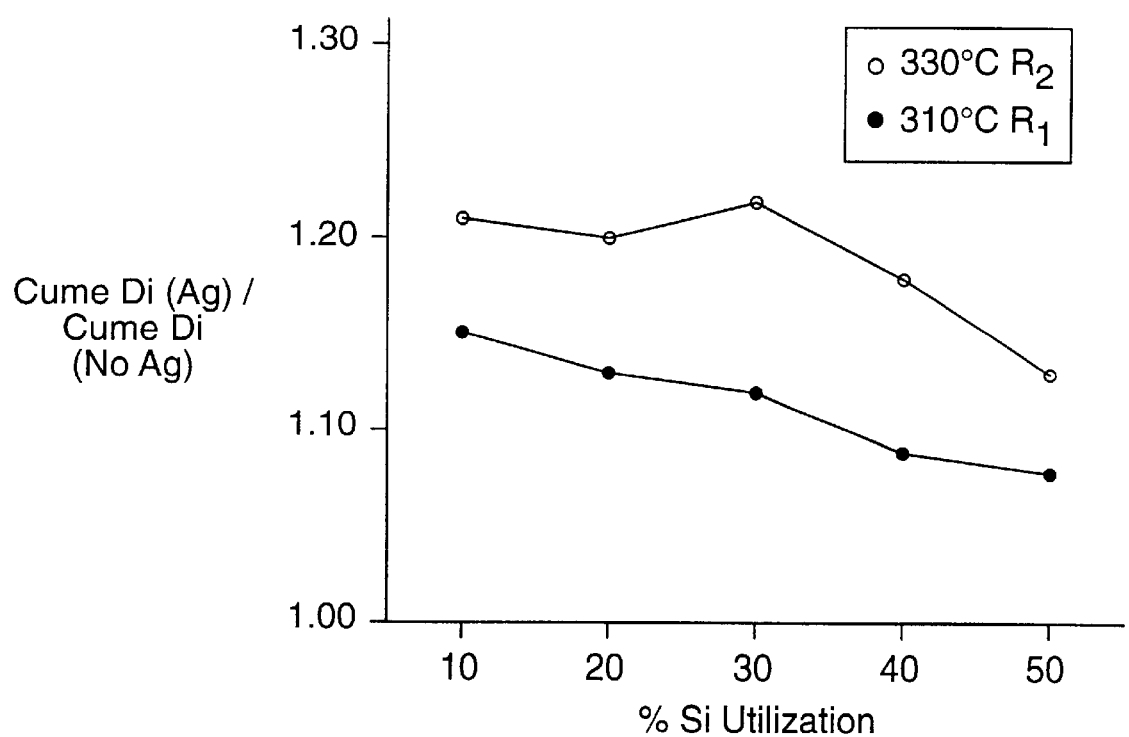
FIG. 8 depicts ratios Cu me Di (Ag added) to Cu me Di (no Ag added) at 310° C. and 330° C., in accordance with embodiments of the present invention.

In Table 1, the "Ag" and "No Ag" columns at 310° C. reaction temperature respectively represent the Cume Di 419 Ag and Cume Di 417 curves of FIG. 1, while the "Ag" and "No Ag" curves at 330° C. reaction temperature respectively represent the Cume Di 421 Ag and Cume Di 420 curves of FIG. 3. The Ag/No Ag ratio at 310° C. (denoted as $R_1$) shows that adding silver increased cumulative D selectivity by about 8% to about 15% at 310° C. The Ag/No Ag ratio at 330° C. (denoted as $R_2$) shows that adding silver increased cumulative D. selectivity by about 13% to about 21% at 330° C. FIG. 8 depicts $R_1$ and $R_2$ as a function of % Si Utilization based on Table 1 and shows that the increase in cumulative D selectivity from adding silver was higher at 330° C. than at 310° C. (i.e., $R_2 > R_1$; D has been increased by the silver addition to a greater extent at 330° C. than at 310° C.). Letting R(T) denote the Ag/No Ag ratio at a reaction temperature T, it was assumed herein that R(T) was a linear function of T, which enabled a determination to be made of the minimum temperature $T_{MIN}$ at which adding silver improves cumulative D selectivity. Defining $T_1$ as 310° C. and $T_2$ as 330° C., and recognizing that $R(T_{MIN})=1$, it followed from the linearity of R(T) that:

$$(T_1 - T_{MIN})/(T_2 - T_1) = (R_1 - 1)/(R_2 - R_1)$$

$$T_{MIN} = T_1 - (T_2 - T_1)(R_1 - 1)/(R_2 - R_1)$$

$$T_{MIN} = 310 - 20(R_1 - 1)/(R_2 - R_1) \quad (1)$$

Figure 10:
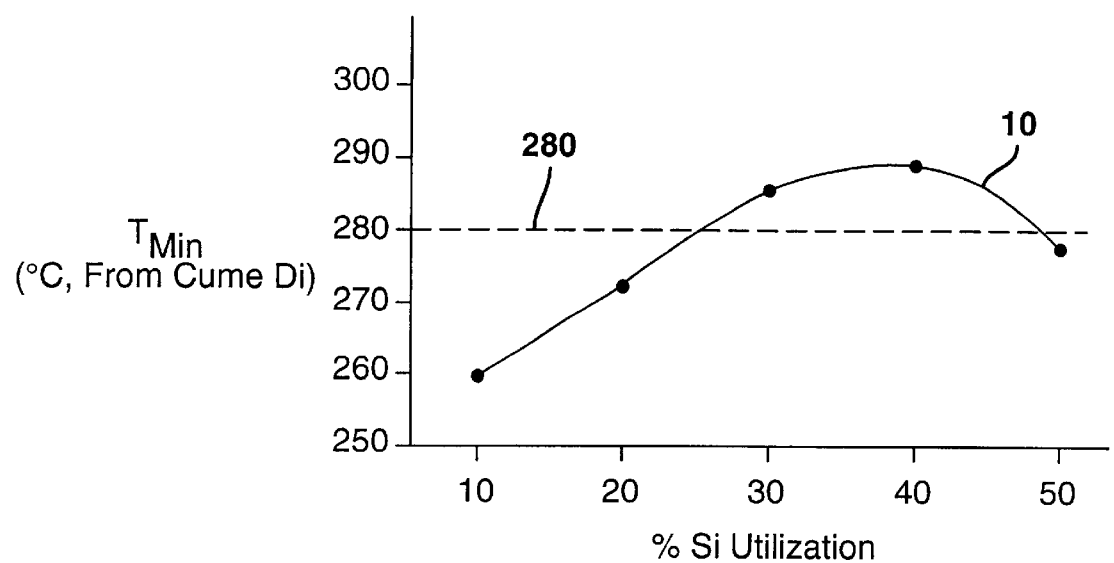
FIG. 10 depicts a minimum temperature ($T_{MIN}$) at which cumulative selectivity for dimethyldichlorosilane is increased by addition of Ag, said selectivity based on a dimethyldichlorosilane weight percent, in accordance with embodiments of the present invention.

Utilizing the $R_1$ and $R_2$ columns as a function of % Si Utilization in Table 1, $T_{MIN}$ was computed from Equation (1) and shown as a column in Table 1. Additionally $T_{MIN}$ was plotted as a function of % Si Utilization in FIG. 10 as a curve 10. In FIG. 10, the reaction temperature of 280° C. was specifically identified as a curve 280, because the minimum reaction temperature at which the chemical reaction took place was about 280° C. Thus, $T_{MIN}$ was considered to be about 280° C. whenever the curve 10 in FIG. 10 was below 280° C. Accordingly, FIG. 10 shows that adding silver promoter increased D selectivity for any reaction temperature at about 280° C. or above when % Si Utilization was in a range between about 10% and about 25%, and for any reaction temperature at 290° C. or above when % Si Utilization was above about 25%. Nonetheless, a production environment may include a range of % Si Utilization that extends outside of about 10% to about 25%. Although such a production environment may include some % Si Utilization outside of about 10% to 25%, the predominant % Si Utilization is likely to be in the about 10% to about 25% range so that adding silver promoter increases net D selectivity (or average D selectivity) for any reaction temperature at about 280° C. or above.

Table 2 summarizes Cume T/D data from FIGS. 2 and 5 as follows.

TABLE 2

| % Si Util. | Reacted At 310° C. (T₁) | | | Reacted At 330° C. (T₂) | | | $T_{MIN}$ ° C.) |
| --- | --- | --- | --- | --- | --- | --- | --- |
| | Ag | No Ag | Ag/No Ag (R₁) | Ag | No Ag | Ag/No Ag (R₂) | |
| 10 | .110 | .187 | .60 | .078 | .195 | .40 | 270 |
| 20 | .113 | .182 | .62 | .105 | .220 | .48 | 263 |
| 30 | .118 | .178 | .66 | .120 | .235 | .51 | 265 |
| 40 | .128 | .176 | .73 | .150 | .255 | .59 | 271 |
| 50 | .145 | .182 | .80 | .195 | .275 | .71 | 266 |

Figure 9:
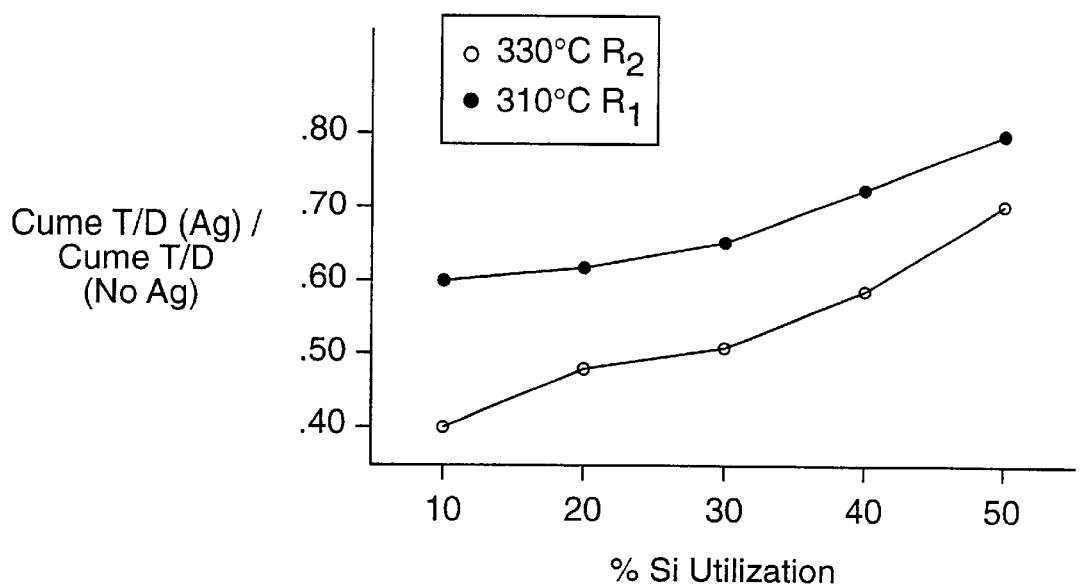
FIG. 9 depicts ratios Cu me T/D (Ag added) to Cu me T/D (no Ag added) at 310° C. and 330° C., in accordance with embodiments of the present invention.

Table 2 and FIG. 9 use definitions of the parameters $T_1$, $T_2$, $R_1$, $R_2$, $T_{MIN}$, and R(T) which are analogous to the definitions used above for these parameters in conjunction with Table 1 and FIG. 8. In Table 2, the "Ag" and "No Ag" columns at 310° C. reaction temperature respectively represent the Cume T/D 419 Ag and Cume T/D 417 curves of FIG. 2, while the "Ag" and "No Ag" curves at 330° C. reaction temperature respectively represent the Cume T/D 421 Ag and Cume T/D 420 curves of FIG. 5. The Ag/No Ag ratio at 310° C. (denoted as $R_1$) shows that adding silver increased cumulative T/D selectivity by about 20% to about 40% at 310° C. The Ag/No Ag ratio at 330° C. (denoted as $R_2$) shows that adding silver increased cumulative T/D selectivity by about 29% to about 60% at 330° C. FIG. 9 depicts $R_1$ and $R_2$ as a function of % Si Utilization based on Table 2 and shows that the increase in cumulative T/D selectivity from adding silver was higher at 330° C. than at 310° C. (i.e., $R_2 < R_1$; T/D has been lowered by the silver addition to a greater extent at 330° C. than at 310° C.). Retaining the definition of R(T) as the Ag/No Ag ratio at a reaction temperature T, the assumption that R(T) was a linear function of T enabled a determination to be made of the minimum temperature $T_{MIN}$ at which adding silver improved cumulative T/D selectivity. Retaining $T_1$ as 310° C. and $T_2$ as 330° C., and recognizing that $R(T_{MIN})=1$ and that R(T) is a linear function of T, Equation (1) applied.

Figure 11:
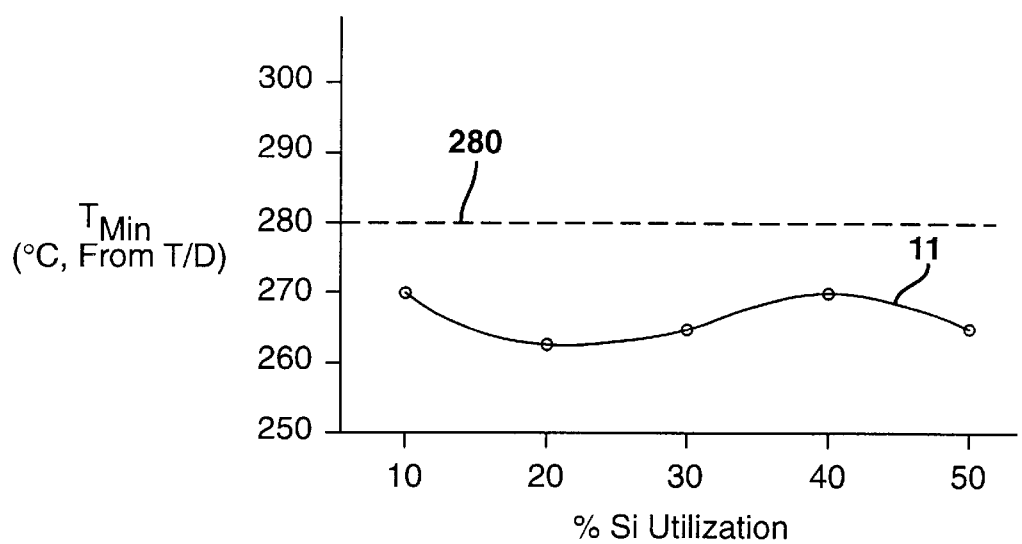
FIG. 11 depicts a minimum temperature ($T_{MIN}$) at which cumulative selectivity for dimethyldichlorosilane is increased by addition of Ag, said selectivity based on a methyltrichlorosilane/dimethyldichlo rosilane weight percent ratio (T/D), in accordance with embodiments of the present invention.

Utilizing the $R_1$ and $R_2$ columns as a function of % Si Utilization in Table 2, $T_{MIN}$ was computed from Equation (1) and shown as a column in Table 2. Additionally $T_{MIN}$ was plotted as a function of % Si Utilization in FIG. 11 as a curve 11. In FIG. 11, the reaction temperature of 280° C. was again specifically identified as the curve 280, because the minimum reaction temperature at which the chemical reaction took place was about 280° C. Thus, $T_{MIN}$ was considered to be about 280° C. whenever the curve 11 in FIG. 11 is below 280° C. Accordingly, FIG. 11 shows that adding silver promoter increased T/D selectivity for any reaction temperature at about 280° C. or above when % Si Utilization is in a range between about 10% and about 50%.

The preceding analysis of Table 1 and Table 2 demonstrates that adding silver promoter increased D selectivity and T/D selectivity, respectively, for a reaction temperature at about 280° C. or above if % Si Utilization was in a range between about 10% and about 50%. Nonetheless, a production environment may include a range of % Si Utilization that extends outside of about 10% to about 50%. Although such a production environment may include some % Si Utilization outside of about 10% to about 50%, the predominant % Si Utilization is very likely to be in the about 10% to about 50% range so that a net D selectivity and T/D selectivity (or average D selectivity and T/D selectivity) will be nonetheless be increased by addition of silver promoter for a reaction temperature at about 280° C. or above.

While the present invention has been described herein with reference to embodiments, those skilled in the art will understand that various changes may be made and equivalents my be substituted for elements thereof without departing from the scope of the present invention. In addition, many modifications may be made to adapt a particular situation or material to the teachings of the present invention without departing from the essential scope thereof. Therefore, the present invention is not intended to be limited to the particular embodiments disclosed herein for carrying out the present invention. The present invention is intended to include all embodiments falling within the scope of the appended claims.

What is claimed is:

1. A method for forming a dialkyldichlorosilane, comprising reacting at a reaction temperature elemental silicon with an alkyl chloride using copper as a catalyst together with promoters zinc, tin, and a special promoter comprising silver, a silver compound, gold, a gold compound, or combinations thereof, wherein the reacting generates the dialkyldichlorosilane in accordance with a first selectivity for the dialkyldichlorosilane that exceeds a second selectivity for the dialkyldichlorosilane, and wherein the second selectivity is a selectivity for the dialkyldichlorosilane that would have existed had the special promoter been absent; and wherein the first selectivity increases as the reaction temperature increases, wherein the second selectivity decreases as the reaction temperature increases, and wherein the reaction temperature is no greater than about 330° C.

2. The method of claim 1, wherein the alkyl of the dialkyldichlorosilane and of the alkyl chloride is selected from the group consisting of methyl, ethyl, n-propyl, n-butyl, isopropyl, isobutyl, sec-butyl, tert-butyl, and n-pentyl.

3. The method of claim 1, wherein the alkyl of the dialkyldichlorosilane and of the alkyl chloride is selected from the group consisting of methyl, ethyl, n-propyl, n-butyl, isopropyl, isobutyl, sec-butyl, tert-butyl, and n-pentyl.

4. The method of claim 1, wherein the copper has weight percent greater than about 5%, based on silicon.

5. The method of claim 1, wherein the special promoter is silver, and wherein the silver has a concentration by weight in a range between about 100 ppm and about 1000 ppm by weight based on silicon.

6. The method of claim 1, wherein the silver compound comprises a silver halide, a silver carbonate, a silver oxide, a silver carbonate, a silver nitrate, or combinations thereof.

7. The method of claim 6, wherein the silver compound includes silver chloride.

8. A method for forming a reaction product mixture, comprising reacting at a reaction temperature elemental silicon with methyl chloride using copper as a catalyst together with promoters zinc, tin, and a special promoter comprising silver, a silver compound, gold, a gold compound, or combinations thereof, wherein the reaction product mixture includes dimethyldichlorosilane and methyltrichlorosilane;

wherein the reacting generates the dimethyldichlorosilane in accordance with a first cumulative selectivity for the dimethyldichlorosilane that exceeds a second cumulative selectivity for the dimethyldichlorosilane, and wherein the second cumulative selectivity is a cumulative selectivity for the dimethyldichlorosilane that would have existed had the special promoter been absent; and wherein the first cumulative selectivity increases as the reaction temperature increases, the second selectivity decreases as the reaction temperature increases, and wherein the reaction temperature is no greater than about 330° C.

9. The method of claim 8, wherein the reacting generates the dimethyldichlorosilane in accordance with a first cumulative selectivity for the dimethyldichlorosilane that exceeds a second cumulative selectivity for the dimethyldichlorosilane, and wherein the second cumulative selectivity is a cumulative selectivity for the dimethyldichlorosilane that would have existed had the special promoter been absent.

10. The method of claim 9, wherein the cumulative selectivity is a Cumulative dimethyldichlorosilane (D) Selectivity.

11. The method of claim 10, wherein the reaction temperature is at least about 280° C.

12. The method of claim 9, wherein the cumulative selectivity is a Cumulative methyltrichlorosilane/dimethyldichlorosilane (T/D) Selectivity.

13. The method of claim 12, wherein the reaction temperature is at least about 280° C.

14. The method of claim 8, wherein the reaction temperature is at least about 300° C.

15. The method of claim 8, wherein the copper has a weight percent greater than about 5% based on silicon, wherein the zinc has a weight percent greater than about 0.5% based on silicon, and wherein the tin has a concentration by weight greater than about 100 ppm by weight based on silicon.

16. The method of claim 8, wherein the copper has a weight percent in a range between about 0.5% and about 20% based on silicon.

17. The method of claim 8, wherein the special promoter is silver, and wherein the silver has a concentration by weight in a range between about 100 ppm and about 1000 ppm by weight based on silicon.

18. The method of claim 8, wherein the silver compound includes silver chloride.

19. The method of claim 8, wherein the reaction product mixture further comprises methyldichlorosilane, wherein the reacting generates a lower weight percent of methyldichlorosilane than a weight percent of methyldichlorosilane that would have been generated had the'special promoter been absent.

20. A chemical mixture used in a chemical reaction that generates a dialkyldichlorosilane, said chemical mixture comprising reactants, a catalyst, and promoters, wherein the reactants include elemental silicon and an alkyl chloride, wherein the catalyst includes copper, wherein the promoters include zinc, tin, and a special promoter comprising silver, a silver compound, gold, a gold compound, or combinations thereof, and wherein the chemical reaction is executed at a reaction temperature;

wherein the chemical mixture has a property that when the chemical mixture is used in the chemical reaction, the dialkyldichlorosilane is generated in accordance with a first selectivity for the dialkyldichlorosilane that exceeds a second selectivity for the dialkyldichlorosilane, and wherein the second selectivity is a selectivity for the dialkyldichlorosilane that would have existed had the special promoter been absent; and wherein the first selectivity increases as the reaction temperature increases, the second selectivity decreases as the reaction temperature increases, and wherein the reaction temperature is no greater than about 330° C.

21. The chemical mixture of claim 20, wherein the alkyl of the dialkyldichlorosilane and of the alkyl chloride is selected from the group consisting of methyl, ethyl, n-propyl, n-butyl, isopropyl, isobutyl, sec-butyl, tert-butyl, and n-pentyl.

22. The chemical mixture of claim 20, wherein the alkyl of the dialkyldichlorosilane and of the alkyl chloride is selected from the group consisting of methyl, ethyl, n-propyl, n-butyl, isopropyl, isobutyl, sec-butyl, tert-butyl, and n-pentyl.

23. The chemical mixture of claim 20, wherein the copper has weight percent greater than 5% based on silicon.

24. The chemical mixture of claim 20, wherein the special promoter is silver, and wherein the silver has a concentration by weight in a range between about 100 ppm and about 1000 ppm by weight based on silicon.

25. The chemical mixture of claim 20, wherein the silver compound comprises a silver halide, a silver carbonate, a silver oxide, a silver carbonate, a silver nitrate, or combinations thereof.

26. The chemical mixture of claim 20, wherein the silver compound includes silver chloride.

27. A chemical mixture used in a chemical reaction that generates a reaction product mixture, said chemical mixture comprising reactants, a catalyst, and promoters, wherein the reactants include elemental silicon and methyl chloride, wherein the catalyst includes copper, wherein the promoters include zinc, tin, and a special promoter comprising silver, a silver compound, gold, a gold compound, or combinations thereof wherein the chemical reaction is executed at a reaction temperature, and wherein a reaction product mixture of the chemical reaction includes dimethyldichlorosilane and methyltrichlorosilane;

wherein the chemical mixture has a property that when the chemical mixture is used in the chemical reaction, the dimethyldichlorosilane is generated in accordance with a first cumulative selectivity for the dimethyldichlorosilane that exceeds a second cumulative selectivity for the dimethyldichlorosilane, and wherein the second cumulative selectivity is a cumulative selectivity for the dimethyldichlorosilane that would have existed had the special promoter been absent; and wherein the first cumulative selectivity increases as the reaction temperature increases, wherein the second selectivity decreases as the reaction temperature increases, and wherein the reaction temperature; is no greater than about 330° C.

28. The chemical mixture of claim 27, wherein the cumulative selectivity is a Cumulative dimethyldichlorosilane (D) Selectivity.

29. The chemical mixture of claim 28, wherein the reaction temperature is at least about 280° C.

30. The chemical mixture of claim 27, wherein the cumulative selectivity is a Cumulative methyltrichlorosilane/dimethyldichlorosilane (T/D) Selectivity.

31. The chemical mixture of claim 30, wherein the reaction temperature is at least about 280° C.

32. The chemical mixture of claim 27, wherein the reaction temperature is at least about 300° C.

33. The chemical mixture of claim 27, wherein the copper has a weight percent greater than about 5% based on silicon, wherein the zinc has a weight percent greater than about 0.5% based on silicon, and wherein the tin has a concentration by weight greater than about 100 ppm by weight based on silicon.

34. The chemical mixture of claim 27, wherein the copper has a weight percent in a range between about 0.5% and about 20% based on silicon.

35. The chemical mixture of claim 27, wherein the special promoter is silver, and wherein the silver has a concentration by weight in arrange between about 100 ppm and about 1000 ppm based on silicon.

36. The chemical mixture of claim 27, wherein the silver compound includes silver chloride.

37. The chemical mixture of claim 27, wherein the reaction product mixture further comprises methyldichlorosilane, wherein the chemical mixture has a property that when the chemical mixtures is used in the chemical reaction a lower weight percent of the methyldichlorosilane is generated than a weight percent of methyldichlorosilane that would have been generated had the special promoter been absent.

* * * * *